United States Patent [19]

Prior et al.

[11] Patent Number: 4,828,989

[45] Date of Patent: May 9, 1989

[54] PROCESS FOR PURIFYING A PROTEIN

[75] Inventors: Chrisopher P. Prior; Garance M. Ducommun, both of Ballwin, Mo.

[73] Assignee: Biogen, Inc., Cambridge, Mass.

[21] Appl. No.: 828,327

[22] PCT Filed: Jun. 4, 1985

[86] PCT No.: PCT/GB85/00236

§ 371 Date: Feb. 4, 1986

§ 102(e) Date: Feb. 4, 1986

[87] PCT Pub. No.: WO85/05637

PCT Pub. Date: Dec. 19, 1985

[30] Foreign Application Priority Data

Jun. 5, 1984 [GB] United Kingdom ............... 8414354

[51] Int. Cl.[4] .................. C12P 21/00; C07K 15/26; A61K 45/02
[52] U.S. Cl. .................................. 435/68; 424/85.5; 530/351; 435/811
[58] Field of Search .............. 424/85, 85.5; 435/811, 435/68; 530/351

[56] References Cited

U.S. PATENT DOCUMENTS

| | | | |
|---|---|---|---|
| 4,175,073 | 11/1979 | Carlsson et al. | 435/178 |
| 4,237,267 | 12/1980 | Okuyama et al. | 435/85 |
| 4,405,601 | 9/1983 | McEntire et al. | 435/240.25 |
| 4,518,526 | 5/1985 | Olson | 424/85 |
| 4,681,930 | 7/1987 | Kung | 435/68 |
| 4,686,284 | 8/1987 | Nara et al. | 435/811 |

OTHER PUBLICATIONS

Chemical Abstracts, vol. 92, Abstract No. 74138x, 1980.

*Primary Examiner*—Blondel Hazel
*Attorney, Agent, or Firm*—James F. Haley, Jr.; Leon R. Yankwich

[57] ABSTRACT

A process for purifying a protein and particularly the purification of a protein, such as gamma interferon, that forms highly insoluble aggregates during the growth of host cells transformed with DNA sequence coding for the protein.

6 Claims, No Drawings

PROCESS FOR PURIFYING A PROTEIN

TECHNICAL FIELD OF THE INVENTION

This invention relates to a process for purifying a protein. More particularly, the invention relates to a process for purifying a protein that forms highly insoluble aggregates during the growth of cells transformed with DNA sequences coding for the protein, the protein being solubilizable and renaturable from the extracts of those cells to produce a conformation that is characterized by less than three surface cysteine amino acid residues.

A preferred protein purified according to the process of this invention is immune or gamma interferon (IFN-γ). The purified, homogeneous and stable gamma interferon produced according to the invention may be utilized in the therapeutic treatment of viral infections, tumors or cancer as well as in immunomodulation applications and methods.

BACKGROUND OF THE INVENTION

Purification procedures such a precipitation, molecular sieve chromatography, electrophoresis, affinity chromatography and covalent chromatography are well known in the art and have been utilized in the purification of proteins from cell extracts. However, purification of proteins produced by cells transformed by recombinant DNA sequences that code for them has posed unique and difficult problems.

Preferably, the level of expression of the recombinant DNA sequence is high and therefore the host cell transformed by that DNA sequence produces a large amount of the desired protein within the cell. Accordingly, the tranformed cell accumulates large numbers of foreign protein molecules. These molecules may then interact with each other to form highly insoluble aggregates, not typically found in the normal cell. The host cell then responds to this unusual accumulation of foreign protein by forming inclusion bodies composed of the foreign protein aggregates. Purification of these foreign proteins in a biologically active form, therefore, requires a means of solubilizing these highly insoluble protein aggregates in such a way to preserve or to enable recovery of their native conformation and a means for purifying the soluble protein in a manner that maintains the biological activity of the protein.

A genetically engineered protein of great value to the health field is interferon. In this application we will use the interferon nomenclature announced in *Nature*, 286, p. 110 (Jul. 10, 1980). "IFN" will designate interferon, "IFN-α" will designate leukocyte interferon, "IFN-β" will designate fibroblast interferon, and "IFN-γ" will designate gamma interferon.

IFN is a cellular protein displaying antiviral activity against a broad range of viruses through induction of cellular RNA and protein synthesis directed against virus replication. For example, human IFN has been used to combat the viral activity of the following: respiratory infections; [*Texas Reports on Biology and Medicine*, Vol. 35, pp. 486-96 (1977) (hereinafter referred to as *Texas Reports*)]; herpes simplex keratitis [*Texas Reports*, pp. 497-500; R. Sundmacher, "Exogenous Interferon In Eye Diseases", *International Virology IV*, The Hague, Abstract nr. w2/11, p. 99 (1978)]; acute hemorrhagic conjunctivitis [*Texas Reports*, pp. 501-510]; adenovirus keraton conjunctivitis [A. Romano et al., ISM MemoI-A8131 (October, 1979)]; varicella-zoster [*Texas Reports*, pp. 511-515]; cytomegalovirus infection [*Texas Reports*, pp. 523-527]; and hepatitis B [*Texas Reports*, pp. 516-522]. See also W. E. Stewart, II, *The Interferon System*, pp. 307-321 Springer-Verlag (2 ed.) (1981) (hereinafter referred to as *The Interferon System*).

IFN has other effects in addition to its antiviral action. For example, it antagonizes the effect of colony stimulating factor, inhibits the growth of hemopoietic colony-forming cells and interferes with the normal differentiation of granulocyte and macrophage precursors [*Texas Reports*, pp. 343-349]. It also inhibits erythroid differentiation in DMSO-treated Friend leukemia cells [*Texas Reports*, pp. 420-428].

IFN may also play a role in the regulation of the immune response. For example, depending upon the dose and time of application in relation to antigen, IFN can be both immunopotentiating and immunosuppressive in vivo and in vitro [*Texas Reports*, pp. 357-369]. In addition, IFN is also known to enhance the activity of killer lymphocytes and antibody-dependent cell-mediated cytotoxicity [R. R. Herberman et al., "Augmentation By Interferon of Human Natural And Antibody-Depenent Cell-Mediated Cytotoxicity", *Nature*, 227, pp. 221-223 (1979); P. Beverley and D. Knight, "Killing Comes Naturally", *Nature*, 278, pp. 119-120 (1979); *Texas Reports*, pp. 375-380; J. R. Huddlestone et al., "Induction and Kinetics of Natural Killer Cells In Humans Following Interferon Therapy", *Nature*, 282, pp. 417-419 (1979); S. Einhorn et al., "Interferon And Spontaneous Cytotoxicity In Man. II. Studies In Patients Receiving Exogenous Leukocyte Interferon", *Acta Med. Scand.*, 204, pp. 478-83 (1978).

Killer lymphocytes and antibody-dependent cell-mediated cytotoxicity may be directly or indirectly involved in the immunological attack on tumor cells. Therefore, in addition to its use as an antiviral agent, IFN has potential application in antitumor and anticancer therapy and in immunomodulation agents and methods [*The Interferon System*, pp. 319-21, 250-56. It is now known that IFNs affect the growth of many classes of tumors in many animals [*The Interferon System*, pp. 292-304.]Interferons, like other antitumor agents, seem most effective when directed against small tumors. The antitumor effects of animal IFN are dependent on dosage and time, but have been demonstrated at concentrations below toxic levels. Accordingly, numerous investigations and clinical trials have been and continue to be conducted into the antitumor and anticancer properties of human IFNs. These include treatment of several malignant diseases such as osteosarcoma, acute myeloid leukemia, multiple myeloma and Hodgkin's disease [*Texas Reports*, pp. 429-35.] Although the reuslts of these clinical tests are encouraging, the antitumor, anticancer and immunomodulation applications of human IFNs have been severely hampered by lack of an adequate supply of purified IFN.

Interferons have been classified into two groups: Type I and Type II IFNs. Type I IFNs are the "classical" acid stable IFNs induced by viruses or synthetic polynucleotides and generally consist of two species: IFN-α and IFN-β. Type II IFN consists of only one species designated as IFN-γ, also referred to in the art as gamma interferon.

IFN-γ is a glycoprotein induced in lymphocytes by specific antigen or various mitogens and is antigenically distinct from IFN-α and IFN-β. [A. Mizrahi et al., "Glycosylation Of Interferon", *J. Biol. Chem.*, 253, pp.

7612–15 (1978); *The Interferon System*, pp. 107–08; P. Gray et al., "Expression Of Human Immune Interferon cDNA In *E. coli* And Monkey Cells", *Nature*, 295, 503–08 (1982); M. P. Langford et al., "Large-Scale Production And Physicochemical Characterization Of Human Immune Interferon", *Infection And Immunity*, 26, pp. 36–41 (1979)]. The protein has been reported to have a molecular weight of 40,000–46,000 daltons, with the possibility that its glycosylated form has a molecular weight of 65,000–70,000 daltons. In addition to being acid labile (at pH2), IFN-γ has been reported to be inactivated after 1 hour at 56° C. See also M. DeLey et al., "Interferon Induced In Human Leukocytes By Mitogens: Prodcution, Partial Purification and Characterization," *Eur. J. Immunol.*, 10, pp. 877–83 (1980); Y. K. Yip et al., "Partial Purification and Characterization Of Human γ (Immune) Interferon", *Proc. Natl. Acad. Sci. USA*, 78, pp. 1601–05 (1981). It has been reported that IFN-γ recognizes a different cell receptor than IFN-α or IFN-β [A. A. Branca et al. "Evidence That Types I And II Interferons Have Different receptors", *Nature*, 294, pp. 768–70 (1981)].

In addition to its antiviral activity, IFN-γ is reported to display antitumor activity. Moreover, as compared to IFN-α and IFN-β, IFN-γ's antitumor activity seems, at least in mice, to result in tumor regression. In addition, its activation of natural killer cells does not reach a plateau, as observed for IFN-α and IFN-β, and IFN-γ appears to be less inhibited by circulating levels of gangliosides than are IFN-α and IFN-β[H. Ankel et al., "Mouse Fibroblast (Type I) And Immune (Type II) Interferons: Pronounced Differences In Affinity for Gangliosides and In antiviral And Antigrowth Effects On Mouse Leukemia L-1210R Cells", *Proc. Natl. Acad. Sci. USA*. 77, pp. 2528–32 (1980). Therefore, it appears that cells or tumors that display poor response to IFN-α or IFN-β may be effectively treated with IFN-γ [e.g., Crane et al., *J. Natl. Cancer Institute*, 61, p. 891 (1978); Barn et al., *Abstract N.Y. Acad. Sci.*, No. II (Oct. 23–26, 1979; Blalock et. al., *Cellular Immunology*, 49, pp, 390–94 (1980); B. Y. Rubin et al., "Differential Efficacies Of Human Type I And Type II Interferons As Antiviral And Antiproliferative Agents", *Proc. Natl. Acad. Sci. USA*, 77, pp. 5928–32 (1980).

Furthermore, it has been suggested that the primary function of IFN-γ may be as an immunoregulatory agent. The antiproliferative effect of IFN-γ on transformed cells has been reported to be 10 to 100 times greater than that of IFN-α or IFN-β [P. W. Gray et al., supra].

Several techniques for the purification of human IFN-γ from human cells have been disclosed. One such technique involves the purification of IFN-γ from cultures of human leukocytes by sequential adsorptions on controlled-pore glass (CPG) and concanavalin A-Sepharose followed by an adsorption on DEAE-Sephacel [Y. K. Yip et al., "Purification of Two Species Of Human γ (lmmune) lnterferon", *Proc. Natl. Acad. Sci. USA*, 79, pp. 1820–24 (1982)]. Another technique is described in U.S. Pat. No. 4,382,027 issued to I. A. Braude on May 3, 1983. IFN-γ is purified to near homogeneity from mitogen-induced human peripheral blood leukocytes by sequential adsorptions on CPG beads, concanavalin A-Sepharose, lentil lectin-Sepharose or pea lectin-agarose, and Heparin-Sepharose or Procian Red-agarose followed by gel filtration chromatography. See also M. P. Langford, supra; M. Wiranowska-Stewart et al., "Production, Partial Purification and Characterization of Human and Murine Interferons - Type II, *Molecular Immunology*, 12, pp. 623–25 (1980); M. deLey et al., supra; Y. K. Yip et al., "Partial Purification And Characterizatiuon of Human γ (Immune) Interferon,"*Proc. Natl. Acad. Sci USA*, 78, pp. 1601–05 (1981); J. A. Georgiades, "Production and Purification of the Human Interferon Gamma (HuIFN-γ)", *Texas Reports on Biology and Medicine*, Vol. 41, pp. 179–83 (1981–82).

Standard methods for the purification of human IFN-γ from human cells require the induction or stimulation of the cells by antigens or mitogens in order to produce sufficient amounts of IFN-γ for purification. See J. A. Georgiades, supra. Even with these purification procedures, however, it is not possible to produce sufficient amounts of IFN-γ for large scale use in clinical trials or in antiviral, antitumor, anticancer or immunomodulation methods and agents.

The technique of genetic engineering, whereby the DNA sequences coding for human IFN-γ are cloned and expressed in a host cell, allows the production of large amounts of the protein. However, as it true for many genetically engineered proteins, the human IFN-γ produced in the host is in the form of highly insoluble protein aggregates. It has proven, therefore, very difficult to isolate and to purify the IFN-γ from the extracts of the variety of hosts in which it it produced. These purification problems have prevented IFN-γ from becoming available in the amounts needed for use in antiviral, anticancer and immunomodulation methods and agents.

DISCLOSURE OF THE INVENTION

This invention solves the problems referred to above by providing a process for the purification of proteins produced by genetic engineering techniques, said proteins forming highly insoluble aggregates during growth of cells transformed with DNA sequences coding for the proteins and being solubilizable and renaturable to produce a conformation that is characterized by less than three surface cysteine residues.

It is a particular object of this invention to provide a means to purify the genetically engineered protein, human IFN-γ, in a stable, native conformation.

It is a further particular object of the invention to provide a purified, homogeneous, stable and non-antigenic preparation of IFN-γ for use in therapeutic treatment in humans.

In that particular embodiment, this invention comprises the steps of: (1) the breakage of cells transformed with DNA sequences coding for IFN-γ and expressing those sequences to such a degree so as to cause the formation within the cell of insoluble multiple aggregates or inclusion bodies containing such aggregates; (2) the extraction of the IFN-γ protein by solubilization with a chaotrope; (3) the renaturation of the soluble protein to its native conformation by rapid dilution or removal of the chaotrope; and (4) the purification of the protein by covalent chromatography on a thiol resin followed by sizing chromatography. The resultant purified IFN-γ in its native conformation can be used therapeutically to combat viral infections, tumors or cancer in man as well as for immunomodulation applications.

Other proteins bearing less than three surface cysteins may be produced and purified in a similar manner in accordance with this invention.

BEST MODE OF CARRYING OUT THE INVENTION

In order that the invention herein described may be more fully understood, the following detailed description is set forth.

The present invention provides a process for the purification of IFN-γ, and other proteins bearing less than three surface cysteine residues, produced in cells transformed with DNA sequences coding for the proteins. The process of the invention provides not only a purified protein product but provides the protein in a stable, native conformation suitable for administration to humans.

In the preferred embodiment of this invention wherein IFN-γ is produced and purified, *E. coli* cells transformed with a plasmid carrying the gene for IFN-γ and expressing the gene in the form of IFN-γ protein are grown in culture. Such cells generally show a degree of expression of IFN-γ ranging from 10–40% of the total cell protein content. This high degree of expression results in the formation of insoluble multiple aggregates within the cell composed of many monomers of IFN-γ bound together through hydrophobic interactions. The bacterial cell typically packages these aggregates into inclusion bodies within the cytoplasm of the cell.

The initial step of the process of the invention requires breakage of these transformed cells to release the IFN-γ-containing inclusion bodies. A cell suspension is first treated with lysozyme, an enzyme that digests the outer peptidoglycan layer of the bacterial cell wall making the cell more vulnerable to osmotic or mechanical disruption. Complete cell breakage is accomplished by mechanical disruption, for example, by the use of a French press or Manton-Gaulin. Centrifugation of the resulting cellular material produces a membrane pellet containing 99% of all the IFN-γ present in the cell, still in the form of multiple aggregates or inclusion bodies. The pellet also contains lipid, lipopolysaccharides, and traces of nucleic acid. Since most *E. coli* proteins are soluble, approximately 70% of the pellet protein is IFN-γ.

The next step of the invention involves the solubilization of the IFN-γ by treatment with a chaotropic agent such as guanidine hydrochloride or urea. These agents are known for their ability to solubilize insoluble protein aggregates. The membrane pellet is homogenized with the chaotrope resulting in the conversion of the multiple aggregates of IFN-γ into soluble individual unfolded protein monomers. Non-solubilized material is removed by centrifugation. It should be noted that treatment with the chaotrope will also solubilize the phospholipids, lipopolysaccarides, and nucleic acids within the pellet as well.

Renaturation of the IFN-γ protein is accomplished by rapid dilution of the chaotrope extract with an aqueous physiological buffer resulting in a net reduction of the chaotrope concentration. The individual IFN-γ monomers refold to a stable native conformation and remain soluble in solution. However, in the case of IFN-γ, it has been found that the protein concentration of the solubilized IFN solution must first be adjusted to approximately 1 mg/ml in order to achieve a satisfactory recovery of soluble native protein upon dilution or removal. A higher protein concentration promotes electrostatic interactions between the monomers upon dilution or removal of the chaotrope which interferes with the refolding and the solubility of the protein. Thus, the chaotrope-containing solubilized IFN solution is initially diluted to a protein concentration of approximately 1 mg/ml with a chaotrope-containing buffer.

Renaturation is then accomplished by the dilution of the chaotrope extract with an aqueous physiological buffer containing PBS (phosphate buffered saline) and a carbohydrate such as sucrose. This dilution step serves two functions: (1) the dilution reduces the chaotrope concentration allowing the protein to refold and (2) the presence of the carbohydrate in the dilution buffer stabilizes the hydrophobic domains of the IFN-γ during refolding of the protein into a native conformation.

Following the dilution step, a 60% recovery of soluble, native protein is achieved. Approximately 40% of the IFN-γ is lost as precipitate which is removed by filtration. This precipitate results from the interaction of poorly refolded IFN-γ molecules with phospholipid and nucleic acid contaminants. Thus, this renaturation step not only provides IFN-γ in a soluble, native form but is a selection mechanism as well, separating the native protein molecules from phospholipid, nucleic acid and protein aggregate contaminants.

A second embodiment of this renaturation step requires the addition of detergent which has a high affinity for solubilized lipid in the extract. The phospholipids in the extract are coated with the detergent and form micelles thus preventing the electrostatic interactions described above which lead to precipitate formation and loss of soluble IFN-γ. The chaotrope can now be removed from the solution by dialysis or diafiltration and the detergents and micelles removed by affinity chromatography.

The filtrate obtained following the renaturation step is approximately 85% pure IFN-γ. However, soluble *E. coli* proteins still contaminate the solution. To purify and concentrate the IFN-γ, the filtrate is subjected to covalent chromatogrpahy utilizing a thiol resin such as activated thiol-Sepharose. Batchwise adsorption is carried out whereby the resin, a Sepharose bead containing a sulfhydryl side chain, is added to the filtrate solution. The solution is stirred and pumped into a column to form a packed column of collected resin.

Since IFN-γ in its native conformation contains two surface cysteines at its amino terminal end, addition of the sulfhydryl-containing resin to the filtrate solution results in oxidation of the sulfhydryl groups on the resin and the IFN-γ to form a disulfide bridge between the two. Thus, the IFN-γ in the solution is covalently bounded to the resin via a disulfide linkage and the remaining proteins in the solution pass through the resin column in the flow-through volume, which is discarded.

It should be noted that this technique is particularly suited to the purification of IFN-γ extracted from *E. coli* cells since *E. coli* proteins generally lack surface cysteine residues and so soluble *E. coli* protein contaminants in the filtrate will not be bound to the resin column. In addition, this procedure selects for IFN-γ in its native conformation which bears a surface cysteine. Any folded protein in which the cysteine is not exposed will not bind to the resin and will pass through the column in the flow-through volume. Furthermore, covalent binding of the IFN-γ protein to the resin adds to the stability of the IFN-γ by promoting further refolding to its native conformation. Although the earlier renaturation step provided an IFN-γ population in a stable, native conformation, the protein at that stage was not fully refolded. Binding of the protein at its amino terminal end to the resin column at this stage immobilizes and anchors the protein so that it can more fully refold to its native conformation. Finally, it should be noted that this step as well as the preceding renaturation step require a protein containing less than three cysteine residues. A greater number of cysteines would promote intermolecular and intramolecular disulfide bridge formation and thus interfere with proper refolding and binding of the protein to the resin.

The bound IFN-γ is eluted from the column with a reductant such as DTT (dithiothreitol) or cysteine. Cystine is preferred since it is non-toxic and it maintains the sulfhydryl groups on the protein in a reduced state, thus preventing aggregation of the protein over time. This covalent chromatography step results in a purified stable IFN-γ population that has been concentrated 10-20 fold over the dilution step.

The final step of the invention involves a second purification via sizing or molecular sieve chromatography. This chromatographic step, however, requires the purified protein to be loaded onto the sizing column in a small volume. Therefore, the protein eluted from the thiol resin column is precipitated with ammonium sulfate, resolubilized in a small volume of formulation buffer and loaded onto the sizing column.

Any large IFN-γ aggregates remaining in the solution are eluted first. The purified IFN-γ is eluted next and collected for further use. E. coli protein contaminants and chemical reagents are eluted last. Thus, this chromatographic step further purifies the IFN-γ preparation by removing any remaining contaminants such as E. coli proteins, protein aggregates, or unwanted chemical reagents such as guanidine hydrochloride, protease inhibitors or reducing agents. In addition, this step allows the exchange of the pure IFN-γ into the appropriate formulation buffer suitable for ultimate therapeutic use in humans. Finally, this purification removes any pyrogen phospholipid which may copurify with IFN-γ and can cause toxic effects if administered to humans at concentrations greater than 1 nanogram.

The pure stable IFN-γ preparation can be diluted to the appropriate doage strength for use in the treatment of viral infections and tumors or cancer in humans.

It is to be understood that the method of this invention may be utilized for purifying any protein produced by genetic engineering techniques which contains less than three surface cysteine amino acid residues and which forms insoluble aggregates within transformed hosts.

In order that this invention may be more fully understood, the following illustrative example of the purification of IFN-γ is set forth.

EXAMPLE

CELL BREAKAGE

E. coli K12 cells transformed with plasmid ptrp-IFN-γ, a plasmid containing the DNA sequence coding for IFN-γ operatively linked to a trp-derived expression control sequence, are grown in culture. One kilogram of these cells is homogenized in 3 liters of buffer #1 (5% sucrose, 0.1 M Tris (pH 7.5) and 5 mM EDTA) using a polytron PT45/80. 0.4 g of lysozyme "powder" is added and the mixture is rehomogenized and allowed to stand at room temperature for 30 min. The sucrose and Tris-containing buffer prevents osmotic lysis of the cells while treatment with lysozyme depletes the cells of the outer peptidoglycan layer of the bacterial cell wall. The "softened cells" are centrifuged at 5,000 rpm for 60 min in a Beckman J6B and the pellet resuspended in 11 liter of buffer #2 (0.1 M Tris (pH 7.5) and 5 mM EDTA) using polytron pT45/80 (setting 5). Suspension of the cells in buffer #2, a hypotonic "break buffer" which lacks sucrose, causes the cells to swell thereby increasing their sensitivity to breakage.

Complete mechanical breakage of the cells is performed by passing the homogenate three times through the Manton-Gaulin at 8,000 psi. The broken cell debris is collected in a cooled 15 liter vessel (kept on ice at approximately 8° C.) and centrifuged at 4,000 rpm for 60 min in a Beckman J6B. A membrane pellet is obtained which is washed by resuspension in 2 liter of buffer #3 (0.5 M urea, 0.2 mM DTT, 10 ml benzamidine and 1x FBS (pH 75. using a polytron PT45/80 (setting 5) followed by centrifugation in the Beckman J6B at 4,000 rpm for 60 min. This wash removes background E. coli proteins. The average weight of the washed membrane pellet is approximately 50 g from 1 kg of cells. IFN-γ is present in the pellet in the form of insoluble multiple aggregates.

EXTRACTION AND RENATURATION OF IFM-γ

Exatraction of stable IFN-γ protein monomers from the membrane pellets requires solubilization of the pellet with a chaotrope. The extracted soluble protein is then renaturated via rapid dilution of the solubilized solution with an aqueous physiological buffer.

50 g of the washed membrane pellet is resuspended in 4.5 liter of 4 M GuHCl (guanidine hydrochloride) extraction buffer (0.2 mM DTT, 10 mM benzamidine, PBS, pH7.2) and left to stand for 30 min at aproximately 8° C. Non-solubilized material is pelleted and discarded by centrifugation in a Beckman J6B at 5,000 rpm for 60 min. The resulting clear supernatant contains solubilized IFN-γ as well as lipids and nucleic acids also contained in the pellet.

In order to reduce the protein concentration of the extract to 1 mg/ml, the optimal concentration for renaturation, the 4 M GuHCl extract is first diluted to 2 M GuHCl by addition of 4.5 liter of PBS buffer (pH 7.2) containing 10% sucrose, 1 mM EDTA, 0.2 mM DTT and 10 mM benzamidine. Samples of the extract are taken to measure the protein concentration using the Biorad Dye Reagent Procedure. The protein concentration at this point typically ranges from 1.5-2.5 mg/ml. The protein concentration is further reduced to 1 mg/ml by addition of the appropriate amount of a 2 M GuHCl solution containing 10% sucrose, 1 mM EDTA, 0.2 mM DTT, 10 mM benzamidine and PBS (pH 7.2). Typically the end volumes of these dilutions range from 10-20 liters. These dilutions are carried out at approximately 8° C.

Renaturation of stable soluble IFN-γ is accomplished by dilution of the 2 M GuHCl extract with a 9-fold volume of PBS dilution buffer (pH 7.2) containing 5% sucrose, 10 mM benzamidine, and 1 mM EDTA at 0°-4° C. The dilution buffer is maintained at 0°-4° C. in a vessel fitted with an ethylene glycol cooling jacket. Aeration of the solution is carefully avoided since this will decrease the yield drastically. This 1/10 dilution results in an approximately 60% recovery of renaturated solouble IFN-γ. About 40% of the IFN-γ precipitates out of solution with lipopolysaccharide and nucleic acid contaminants. The fine precipitate is removed by filtering the volume (100–200 liters) through a Millipore CV6LO1TP1 10 inch 0.22 mm hydrophilic TC duropore filter. A sample is taken here to measure protein concentration using the Biorad method. The protein concentration at this stage is typically 0.055 mg/ml.

PURIFICATION OF IFN-γ VIA COVALENT CHROMATOGRAPHY

The dilution mixture containing renatured IFN-γ is next subjected to covalent chromatography utilizing a thiol resin. To facilitate the disulphide bridge formation by which the IFN-γ protein binds to the resin, the "dilution" mixture is first adjusted to pH 8 with 1 N NaOH. Activated thiol Sepharose 4B (Pharmacia Fine Chemicals) is added batchwise (2% vol/vol) and stirred for at least 2–3 h or overnight at 4° c. The thiol resin is prepared as recommended by the manufacturer, i.e., washing with 10 volumes of distilled water followed by equilibration in 5 volumes of PBS buffer (pH 8.0) containing 0.2 M GuHCl, 5% sucrose, 10 mM benzamidine, and 5 mM EDTA. The IFN-γ, through its surface cysteine residues, will covalently bind to the sulfhydryl side chain on the resin.

After the batch adsorption, the activated thiol Sepharose 4B is pumped into a Pharmacia column (KS370/15) at a flow rate of 200 liters/h. The flow-through volume of eluant is measured for protein concentration from which the amount of protein binding to the column resin can be determined. The packed resin column is washed with 5 volumes of PBS buffer (pH 8.0) containing 0.2 M GuHCl, 10 mM benzamidine, 5mM EDTA, and 5% sucrose at a flow rate of 40 liters/h. Elution of the bound IFN-γ is accomplished by allowing the washed beads to stand in 2 volumes of elution buffer containing PBS (pH 8.0), 40 mM of the reductant DTT or cysteine, 5% sucrose, 5 mM EDTA, and 10 mM benzamidine for 4 h or overnight at 4° C. The released IFN-γ in the eluant is collected at a flow rate of 30 liter/h. The elution is continued by allowing the beads to stand in a further 1 volume of elution buffer at 4° C. for 30 min. and fractions are collected until the protein concentration goes below 0.1 mg/ml.

FINAL PURIFICATION OF IFN-γ VIA SIZING CHROMATOGRAPHY

The IFN-γ eluted off the thiol resin column must be concentrated in a smaller volume for loading onto a molecular sizing column. Thus, 400 g of solid ammonium sulphate is dissolve in 1 liter of IFN-γ solution and allowed to stand overnight at 4° C. The protein precipitate that results is pelleted by centrifugation in a Abeckman J6B at 5,000 rpm for 60 min at 4° C. and then dissolved in 250 ml volume for formulation buffer containing PBS (pH 7.2) and 5% sucrose. Undissolved material is removed by centrifugation in a Sorvall GSA rotor equipped for 250 ml buckets at 12,000 rpm, for 30 min.

The Clear IFN-γ solution (250 mls at approximately 15 mg/ml) is applied to a 10 liter S-200 Sephadex sizing column (K100/100) at 4° C. at a flow rate of approximately 500 ml/h. The elution of materials off the column may be monitored by SDS-polyacrylamide gel electrophoresis and the fractions containing pure IFN-γ pooled for further use. The IFN-γ is eluted with approximately 50% of the column volume and 100 ml fractions are collected.

This procedure results in a pure stable IFN-γ preparation still in the formulation buffer which can be diluted to an appropriate dose strength with additional formulation buffer.

While a number of embodiments of this invention are presented hereinabove, it is apparent that the basic construction can be altered to provide other embodiments which utilize the process of this invention. Therefore, it will be appreciated that the scope of this invention is to be governed by the claims appended hereto rather than the specific embodiments which have been presented hereinabove by way of example.

We claim:

1. A process for the purification of a *human gamma interferon* protein bearing less than three surface cysteine residues, which forms highly insoluble aggregates during the growth of cells transformed with DNA sequences coding for the protein, comprising the steps of: (a) breaking said transformed cells, (b) extracting said protein by solubilization of the protein with a chaotrope (C) renaturing said protein by rapid dilution or removal of the chaotrope, and (d) purifying said protein by covalent chromatography on a thiol resin followed by molecular sizing chromatography to obtain said protein in its native conformation.

2. A process for the purification of IFN-γ from inclusion bodies formed during the growth of cells transformed with DNA sequences coding for IFN-γ, comprising the steps;
   (a) breaking the cells,
   (b) extracting the IFN-γ by solubilization with a chaotrope,
   (c) adjusting the chaotrope containing solubilized IFN-γ solution formed in step (b) to an IFN-γ concentration of approximately 1 mg/ml with a chaotrope-containing buffer,
   (d) renaturing the IFN-γ by dilution of the chaotrope extract with aqueous phsyiological buffer containing phosphate buffered saline and carbohydrate, optionally also containing a detergent having affinity for solubilized lipid in said extract,
   (e) purifying the IFN-γ by (i) covalent chromatography on a thiol resin capable of forming disulfide linkages with the surface cysteines of said IFN-γ, and thereafter (ii) molecular sizing chromatography, and
   (f) recovering IFN-γ in its native conformation.

3. The process according to claim 2, wherein the chaotrope is urea or guanidine hydrochloride.

4. The process according to claim 2, wherein said carbohydrate is sucrose.

5. The process according to claim 2, wherein the IFN-γ is eluted from the thiol resin with a reductant.

6. The process according to claim 5, wherein said reductant is dithiothreitol or cysteine.

* * * * *